United States Patent [19]

Köppe et al.

[11] 4,256,756
[45] Mar. 17, 1981

[54] 1-ARYLOXY-2-HYDROXY-3-[(SUBSTITUTED PHENYL-DONIDAZALIDINON-2-YL)-ALKYL-AMINO]-PROPANES AND SALTS THEREOF

[75] Inventors: Herbert Köppe, Ingelheim am Rhein; Anton Mentrup, Mainz-Kastel; Ernst-Otto Renth; Kurt Schromm, both of Ingelheim am Rhein; Wolfgang Hoefke, Budenheim; Gojko Muacevic, Ingelheim am Rhein, all of Fed. Rep. of Germany

[73] Assignee: Boehringer Ingelheim GmbH, Ingelheim am Rhein, Fed. Rep. of Germany

[21] Appl. No.: 4,279

[22] Filed: Jan. 17, 1979

Related U.S. Application Data

[63] Continuation-in-part of Ser. No. 838,450, Oct. 3, 1977, abandoned.

[30] Foreign Application Priority Data

Oct. 5, 1976 [DE] Fed. Rep. of Germany ....... 2644833

[51] Int. Cl.² .................. A61K 31/415; C07D 233/36
[52] U.S. Cl. ................................ 424/273 R; 548/318; 548/320; 548/305; 548/229; 544/105; 546/158; 424/248.56; 424/248.58; 424/258; 424/273 B; 260/239 A
[58] Field of Search .............................. 548/320, 318; 424/273 R

[56] References Cited

U.S. PATENT DOCUMENTS

3,852,291 12/1974 Augstein et al. .................... 548/320
4,154,829 5/1979 Mentrup et al. .................. 424/273 R

FOREIGN PATENT DOCUMENTS

2109651 9/1971 Fed. Rep. of Germany ........... 548/305
2234332 2/1973 Fed. Rep. of Germany ........... 548/305

OTHER PUBLICATIONS

Maruyama et al., Chem. Abst. 1974, vol. 81, No. 105507w.
Bond et al., Chem. Abst. 1967, vol. 67, No. 81991g.

*Primary Examiner*—Alan L. Rotman
*Assistant Examiner*—Natalia Harkaway
*Attorney, Agent, or Firm*—Hammond & Littell, Weissenberger & Muserlian

[57] ABSTRACT

Compounds of the formula

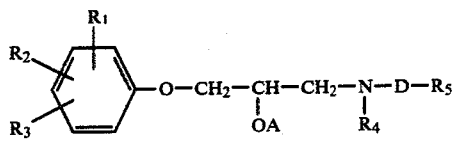

wherein
$R_1$, $R_2$ and $R_3$ are hydrogen or substituents of various types;
$R_4$ is hydrogen; alkyl of 1 to 5 carbon atoms; or optionally substituted aralkyl of 7 to 14 carbon atoms;
$R_5$ is a heterocycle;
D is alkylene of 1 to 12 carbon atoms; and
A is hydrogen or acyl;

and non-toxic, pharmacologically acceptable acid addition salts thereof. The compounds as well as their salts are useful as α- and β-adrenergic receptor blocking agents and antidepressants.

8 Claims, No Drawings

1-ARYLOXY-2-HYDROXY-3-[(SUBSTITUTED PHENYL-DONIDAZALIDINON-2-YL)-ALKYL-AMINO]-PROPANES AND SALTS THEREOF

This is a continuation-in-part of copending application Ser. No. 838,450 filed Oct. 3, 1977 now abandoned.

This invention relates to novel 1-aryloxy-2-hydroxy-3-[heterocyclic-substituted alkyl)-amino]-propanes and non-toxic acid addition salts thereof, as well as to various methods of preparing these compounds.

More particularly, the present invention relates to a novel class compounds represented by the formula

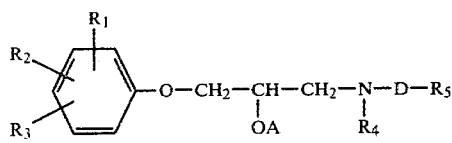

wherein $R_1$ is hydrogen; halogen; trifluoromethyl; nitro; alkyl of 1 to 8 carbon atoms; alkoxy of 1 to 4 carbon atoms; alkoxyalkyl of 2 to 8 carbon atoms; alkenyl of 2 to 5 carbon atoms; alkynyl of 2 to 5 carbon atoms; alkenyloxy of 3 to 6 carbon atoms; alkynyloxy of 3 to 6 carbon atoms; optionally bridged and/or unsaturated cycloalkyl of 3 to 12 carbon atoms; optionally bridged and/or unsaturated cycloalkoxy of 3 to 12 carbon atoms; —$(CH_2)_x$—A′, where x is 0, 1, 2 or 3 and A′ is cyano, amino, carboxamido or hydroxyl; —$COOR_6$, where $R_6$ is hydrogen or alkyl of 1 to 4 carbon atoms; low-molecular aliphatic, araliphatic or aromatic acyl, acyloxy or acylamino; —NH—CO—$NR_7R_8$ or —O—CO—$NR_7R_8$, where $R_7$ and $R_8$ are each hydrogen or alkyl or, together with each other and the adjacent nitrogen atom, form a heterocycle such as pyrrolidino, piperidino or morpholino; aryl (preferably phenyl), aryloxy (preferably phenoxy) or aralkoxy (preferably benzyloxy), each optionally having one or more substituents selected from the group consisting of halogen, alkyl, nitro, cyano, and carboxyl attached thereto; —NH—$R_9$ or N-alkylene-$R_9$, where $R_9$ is lower alkyl or acyl such as $CH_3SO_2$—, $(CH_3)_2N$—$SO_2$— or alkyl—O—CO—; —CO—NH—alkyl; —CO—NH—$NH_2$; —$CH_2$—$SO_2$—$CH_3$; —CO—NH—OH; or —CO—N(alkyl)$_2$;

$R_2$ is hydrogen, halogen, alkyl of 1 to 4 carbon atoms; alkoxy of 1 to 4 carbon atoms, aralkoxy of 7 to 14 carbon atoms, preferably benzyloxy; alkenyl of 2 to 4 carbon atoms; cyano; nitro; hydroxyl; amino; or, together with $R_3$, —O—$CH_2$—O, O—$(CH_2)_2$—O, —CH=CH—CH=CH—, O—$CH_2$—CONH—, —$(CH_2)_2$—CONH—, —CH=CH—NH—, O—CO—NH—, —$CH_2$—CH=CH—$CH_2$—, —O—CH=CH—, —O—$(CH_2)_3$—, —S$(CH_2)_3$— or —CO$(CH_2)_3$—, preferably attached to carbon atoms of the phenyl ring in o-position with respect to each other;

$R_3$ is hydrogen; halogen; alkyl of 1 to 4 carbon atoms; alkoxy of 1 to 4 carbon atoms, aralkoxy of 7 to 14 carbon atoms; preferably benzyloxy; or hydroxyl;

$R_4$ is hydrogen, alkyl of 1 to 5 carbon atoms; or optionally substituted aralkyl of 7 to 14 carbon atoms;

$R_5$ is

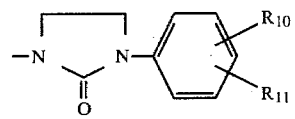

where $R_{10}$ and $R_{11}$ are each hydrogen, halogen, alkyl of 1 to 4 carbon atoms, alkoxy of 1 to 4 carbon atoms, trifluoromethyl, carboxamido or, together with each other, —O—$(CH_2)_y$—O—, where y is 1 or 2, attached to carbon atoms of the phenyl ring in o-position with respect to each other;

or

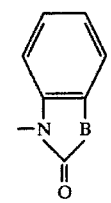

where B is

where $R_{12}$ is optionally substituted aryl; —O—$CH_2$—, where the oxygen atom is attached to the phenyl ring; or —$(CH_2)_2$—;

D is alkylene of 1 to 12 carbon atoms; and

A is preferably hydrogen or also acyl, especially the particular acyl radicals mentioned in the definition of $R_1$;

and non-toxic, pharmacologically acceptable acid addition salts thereof.

Examples of particular embodiments of alkyl and alkoxy substituents included in the definition of $R_1$, $R_2$ and $R_3$ are primarily methyl, ethyl, isopropyl, methoxy, ethoxy and isopropoxy.

Examples of particular embodiments of alkenyl, alkynyl, alkenyloxy and alkynyloxy substituents included in the definition of $R_1$ are vinyl, allyl, ethynyl, allyloxy and propargyloxy.

Examples of particular embodiments of cycloalkyl and cycloalkoxy substituents included in the definition of $R_1$ are cyclopropyl, cyclopentyl, cyclopentyloxy and adamantyl.

Examples of particular embodiments of halogen substituents included in the definition of $R_1$, $R_2$ and $R_3$ are fluorine, chlorine, bromine as well as iodine.

Examples of particular embodiments of acyl substituents included in the definition of $R_1$ and A are acetyl, propionyl, butyryl, isobutyryl, phenacetyl, benzoyl and naphthoyl, where each of the aromatic acyl radicals may optionally have one or more halo, lower alkyl, nitro, cyano and/or carboxyl substituents attached to the aromatic moiety.

In those instances where $R_1$ ia acyloxy or acylamino, examples of particular embodiments of the acyl moieties thereof are the same as those referred to in the preceding paragraph.

When $R_3$ and $R_2$ together with each other are —O—$CH_2$—O—, the preferred embodiment thereof is 3,4-methylenedioxy.

Finally, examples of particular embodiments of D are ethylene, trimethylene, tetramethylene, hexamethylene, dodecamethylene, 1-methyl-ethylene, 2-methyl-ethylene, 1,1-dimethyl-ethylene, 1,1-dimethyl-propylene, 1,1-dimethyl-butylene and 1,1,4,4-tetramethyl-butylene.

The compounds of this invention comprise at least one asymmetric carbon atom, namely that in the —CHOA— group of the propane side-chain, and therefore occur in racemic or optically active forms. The separation of the racemates into their optically active isomer components may be effected in conventional manner, for instance with the aid of optically active auxiliary acids such as dibenzoyl- or di-p-toluyl-D-tartaric acid, D-3-bromo-camphor-sulfonic acid or (—)-2,3,4,5-di-O-isopropylidene-2-keto-L-gluconic acid, where a solubilizing agent such as allylamine in petroleum ether may be added, for instance after the first crystallization. The optically active compounds may, however, also be obtained by using optically active starting material. It should further be pointed out that the pharmacological activities of the compounds of this invention, especially the β-adrenergic receptor blocking activity, are as usual more pronounced in that optically active form which exhibits the absolute "S"-configuration.

The compounds embraced by formula I are organic bases and therefore form acid addition salts with inorganic or organic acids. Examples of non-toxic, pharmacologically acceptable acid addition salts are those formed with hydrochloric acid, hydrobromic acid, phosphoric acid, sulfuric acid, methanesulfonic acid, maleic acid, acetic acid, oxalic acid, lactic acid, tartaric acid, 8-chlorotheophylline, salicylic acid, citric acid, β-naphthoic acid, adipic acid, 1,1-methylene-bis-(2-hydroxy-3-naphthoic acid), an acid synthetic resin such as sulfonated ploystyrene resin, or the like.

The compounds of the present invention may be prepared by various methods utilizing known chemical synthesis principles for the preparation of 1-aryloxy-2-hydroxy-3-substituted amino-propanes. Thus, the synthesis of the novel compounds is effected by building the molecule from the following four building radicals:

1. An aryloxy radical of the formula

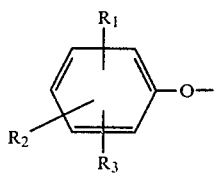

where $R_1$, $R_2$ and $R_3$ have the same meanings as in formula I;

2. A (optionally esterified) 2-hydroxypropylene side-chain of the formula

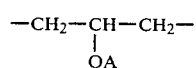

where A has the same meanings as in formula I;

3. An imino radical of the formula $>NR_4$ where $R_4$ has the same meanings as in formula I; and 4. A heterocyclic-substituted alkyl radical of the formula

—D—$R_5$ where D and $R_5$ have the same meanings as in formula I.

In principle, the various intermediate steps can be performed in any desired sequence.

More particularly, the compounds of this invention may be prepared by the following methods:

Method A

By reacting a compound of the formula

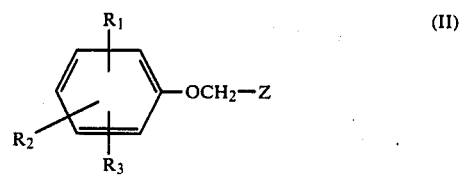

wherein $R_1$, $R_2$ and $R_3$ have the same meanings as in formula I, and

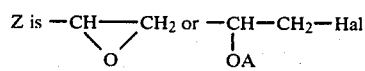

where Hal is halogen, and

A has the same meanings as in formula I, with an amine of the formula $HNR_4$—D—$R_5$     (III)

wherein $R_4$, $R_5$ and D have the same meanings as in formula I.

The starting compounds of the formula II may be obtained by reacting a phenol of the formula

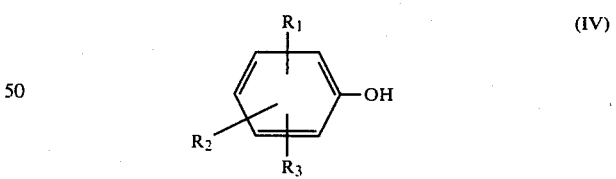

wherein $R_1$, $R_2$ and $R_3$ have the same meanings as in formula I, that is, a compound comprising the building radical No. 1 above, with epichlorohydrin, that is, a compound comprising a building radical No. 2 above.

In the other methods of preparation described below the starting compounds and synthesis step also utilize the building radicals Nos. 1 to 4 set forth above, but their identity will not be particularly referred to because it will be obvious to those skilled in the art.

Method B

By reductive amination of a compound of the formula

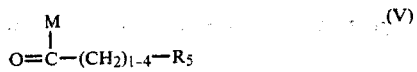   (V)

where M is hydrogen or methyl, and $R_5$ has the same meanings as in formula I, with a primary amine of the formula

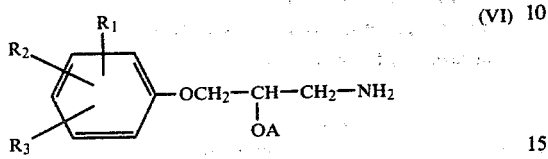   (VI)

wherein $R_1$, $R_2$, $R_3$ and A have the same meanings as in formula I, using a conventional hydrogenating agent such as lithium aluminum hydride or SDMA, or catalytically activated hydrogen.

The starting compound for the synthesis pursuant to this method may also be the intermediate Schiff's base of the formula

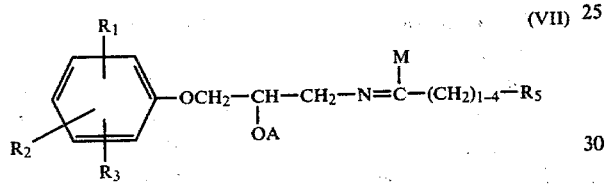   (VII)

wherein $R_1$, $R_2$, $R_3$ and $R_5$ have the same meanings as in formula I, and M has the same meanings as in formula V.

This method, however, is less suitable for the preparation of compounds of the formula I where substituents $R_1$, $R_2$ and/or $R_3$ comprise bonds which are likely to be attacked by reducing agents, that is, an unsaturated carbon-to-carbon bond, a C≡N bond or a C=O bond.

Method C

By reacting a phenol of the formula IV with an azetidinol of the formula

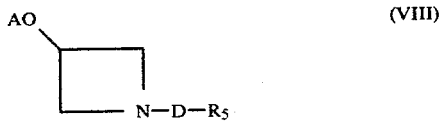   (VIII)

wherein A, D and $R_5$ have the same meanings as in formula I.

Method D

By condensing an amine of the formula

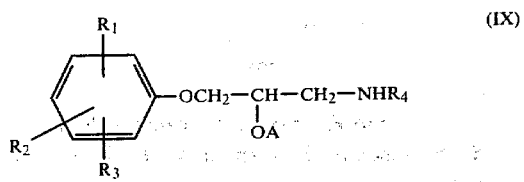   (IX)

where $R_1$ through $R_4$ and A have the previously defined meanings, with a compound of the formula $$X-D-R_5 \quad (X)$$

wherein $R_5$ and D have the previously defined meanings, and X is an ester group which is easily removable as an anion, such as halogen, mesyl or tosyl.

Method E

By hydrolytic oxazolidine cleavage of a compound of the formula

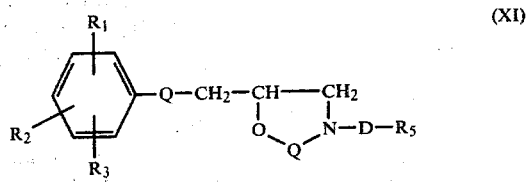   (XI)

where $R_1$ through $R_3$, D and $R_5$ have the meanings previously defined, and Q is —$CH_2$— or —CO—. This method leads only to compounds of the formula I wherein $R_4$ and A are hydrogen.

Method F

By removing the protective group from a compound of the formula

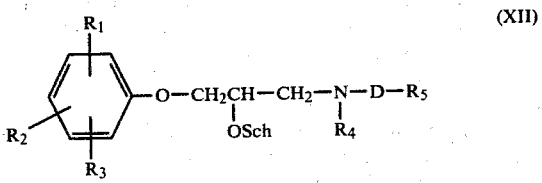   (XII)

where $R_1$ through $R_5$ have the meanings previously defined, and Sch is a conventional protective group, for example, one of the acyl substituents included in the definition of $R_1$, benzyl or an acetal group, which leads to a compound of the formula I, wherein A is hydrogen.

The removal of the protective group may be effected by hydrolysis in an aqueous alkaline or acid medium, or by hydrogenation, for instance with catalytically activated hydrogen. However, the hydrogenation method cannot be applied to compounds containing substituents which are subject to reduction.

Other methods for preparing the compounds of the present invention involve the conversion of one or more of substituents $R_1$, $R_2$, $R_3$, $R_4$, $R_{10}$ and $R_{11}$ having a meaning defined above into another type of substituent included in their respective definitions. The following methods are illustrative thereof:

Method G

Catalytic hydrogenation of a compound of the formula I wherein $R_4$ is arylmethyl to form a corresponding compound where $R_4$ is hydrogen. This method is also applicable only to the preparation of compounds of the formula I comprising substituents $R_1$, $R_2$ and/or $R_3$ which are unaffected by catalytically activated hydrogen.

Method H

Catalytic hydrogenation or ether cleavage of a compound of the formula I wherein at least one of substituents $R_1$, $R_2$ and $R_3$ is benzyloxy, to form a corresponding compound of the formula I wherein at least one of the corresponding substituents $R_1$, $R_2$ and $R_3$ is hydroxyl. The ether cleavage may be effected by means of a hydrohalic acid or a borontrihalide. The catalytic hydrogenation method may be applied only to those compounds of the formula I wherein $R_1$, $R_2$, $R_3$ and/or $R_5$ are substituents which are unaffected by catalytically activated hydrogen.

Method I

Aminolysis of a compound of the formula I wherein $R_1$ is —COO—alkyl, to form a corresponding compound of the formula I wherein $R_1$ is —CONH$_2$, —CONH—alkyl, —CON(alkyl)$_2$, —CO—NHNH$_2$ or —CONHOH.

Method K

Halogenation of a compound of the formula I wherein at least one of substituents $R_1$, $R_2$, $R_3$, $R_{10}$ and $R_{11}$ is hydrogen, for example with a hydrohalic acid in the presence of hydrogen peroxide. By using only one equivalent of hydrohalic acid/H$_2$O$_2$, the halogen substitution may be restricted to an aryl group.

Method L

Alkylation of a compound of the formula I wherein $R_4$ is hydrogen, to form a corresponding compound of the formula I wherein $R_4$ is alkyl, with the aid of a conventional alkylation agent such as an alkyl halide, mesylate or tosylate, or in case of introduction of a methyl group with formaldehyde/formic acid.

Method M

Conversion of a compound of the formula I wherein $R_1$ is primary amino into a corresponding compound of the formula I wherein $R_1$ is halogen or cyano, by means of the Sandmeyer-reaction, that is, by diazotizing and treating with a copper-I-halide or -cyanide.

Method N

Reduction of a compound of the formula I wherein $R_1$ is a group convertible into another group included in the definition of $R_1$ by reduction, such as —NO$_2$ or —COO—alkyl, to form a corresponding compound of the formula I wherein $R_1$ is a group producible by reduction, such as —NH$_2$ or —CH$_2$OH. This method is also applicable only to compounds of the formula I wherein substituents $R_2$ and/or $R_3$ are not subject to reduction.

Method O

Ether cleavage of a compound of the formula I wherein at least one of substituents $R_1$, $R_2$ and $R_3$ is lower alkoxy, preferably methoxy, to form a corresponding compound of the formula I wherein at least one of substituents $R_1$, $R_2$ and $R_3$ is hydroxyl, by means of a concentrated hydrohalic acid.

Most of the compounds of the formulas II, V to VII, IX, XI and XII used as intermediate products are known; those which are not known may be obtained by known methods from compounds of the formulas III and IV. Phenols of the formula IV are known or else are easily accessible by known methods. The intermediates of the formulas III, VIII and X, on the other hand, have not yet been described in the literature. Therefore, methods for their preparation will be described below, especially because they are starting compounds for methods A, C and D which are most interesting, from an economic point of view, for the preparation of the final products according to the invention.

Compounds of the formula III may be prepared
(a) by reduction of a nitro compound of the formula $$NO_2-D-R_5 \quad (XIII)$$

where D and $R_5$ have the meanings previously defined. This process leads to those compounds of the formula III where $R_4$ is hydrogen;

(b) by removing one or two protective groups from a compound of the formula

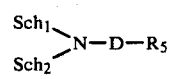

(XIV)

wherein D has the meanings previously defined, Sch$_1$ is a conventional protective group such as acyl, —COO—E, where E is alkyl, arylmethyl or aryl, or arylmethyl, and Sch$_2$ has the same meaning as Sch$_1$, but may in addition also be hydrogen or, together with Sch$_1$, CH-E where E has the above defined meanings, or the radical of a dicarboxylic acid such as succinyl or phthalyl.

If desired, an alkyl substituent of 1 to 5 carbon atoms or an aralkyl substituent of 7 to 14 carbon atoms may be attached by conventional methods to the amino moiety of a compound obtained pursuant to (a) or (b) above.

The starting compounds of the formula X which have the structure

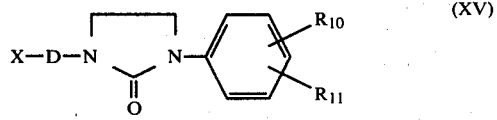

(XV)

where D, $R_{10}$, $R_{11}$ and X have the meanings previously defined, may be prepared by reacting an oxazolidinone of the formula

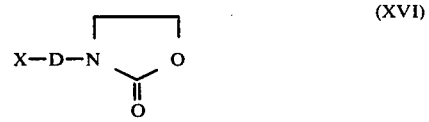

(XVI)

where X and D have the meanings defined above, with an isocyanate of the formula

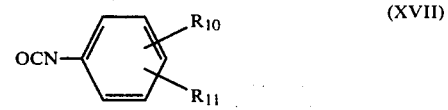

(XVII)

where $R_{10}$ and $R_{11}$ have the meanings defined above.

Compounds of the formula VIII where A is hydrogen may be prepared, for example, by reacting a compound of the formula III with epichlorohydrin.

Starting compounds of the formula X which have the structure

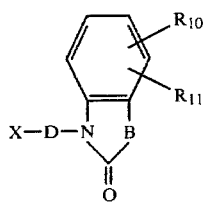

(XVIII)

where X, D, B, $R_{10}$ and $R_{11}$ have the above-defined meanings, may be obtained from a compound of the formula

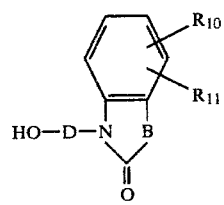

(XIX)

where D, B, $R_{10}$ and $R_{11}$ have the meanings defined above, which is itself prepared by cyclization of a compound of the formula

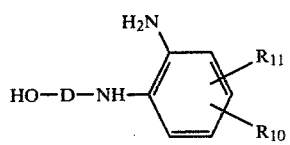

(XX)

where D, $R_{10}$ and $R_{11}$ have the above-defined meanings, by treating the same with a conventional halogenation agent such as $SOCl_2$ or $POCl_3$. It is also possible to introduce the side chain X—D— into a compound of the formula

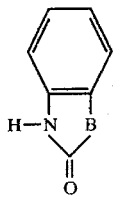

(XXI)

by means of a dihalo-alkylene of the formula $$X_2-D-X_1 \quad (XXII)$$

differently activated at both ends, where D has the previously defined meanings, and $X_1$ as well as $X_2$ are halogens, but $X_2$ has a higher atomic weight than $X_1$, for example by means of an α-bromo-ω-chloro-alkylene.

The following examples illustrate the present invention and will enable others skilled in the art to understand it more completely. It should be understood, however, that the invention is not limited solely to the particular examples given below.

EXAMPLE 1

1-(α-Naphthoxy)-3-[1,1-dimethyl-3-(N-benzimidazolone-(2)-yl)-propylamino-(1)]-propanol-(2) hydrochloride monohydrate by method A A mixture consisting of 3 gm of 1-(3-amino-3,3-dimethyl-n-propyl)-benzimidazolidinone-(2), 3.3 gm of 1-[naphthyl-(1)-oxy]-propylene-(2,3)-epoxide and 12 ml of 98% ethanol was refluxed for three hours. Thereafter, the ethanol was distilled off, the residue was taken up in some methanol, and the solution was acidified with 1 N hydrochloric acid and then extracted with ethyl acetate. The ethyl acetate was distilled out of the extract solution, and ether and some water were added to the residue, whereupon a crystalline substance separated out. The product was recrystallized from ethanol, yielding 60% of theory of the compound of the formula

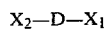

which had a melting point of 161° C.

Using a procedure analogous to that described in Example 1, the following additional compounds of the indicated formula were prepared by refluxing the corresponding epoxide of the formula II with the corresponding aminoalkyl compound of the formula III in 98% ethanol:

TABLE I

Structure: Ar-OCH₂-CHOH-CH₂-NH-D-N(B)-benzoxazolone where Ar has substituents R₁, R₂, R₃

| R₁ | R₂ | R₃ | D | B | m.p. °C. (salt) |
|---|---|---|---|---|---|
| H | 2,3-CH=CH—CH=CH— | | (CH₃)₂C—CH₂— | —NH— | 217 (hydrochloride) |
| 2-Cl | H | H | " | " | 214 (hydrochloride) |
| 2-Cl | H | H | —(CH₂)₂— | " | 169 (maleate) |
| 2-Cl | H | H | " | —OCH₂— | 153 (p-aminobenzoate) |
| 2-Cl | H | H | (CH₃)₂C(CH₂)₂— | —NH— | 166 (maleate) |
| H | 2,3-CH=CH—CH=CH— | | " | —OCH₂— | 125 (hydrochloride monohydrate) |
| H | " | | " | —(CH₂)₂— | 95 (hydrochloride monohydrate) |
| 3-CH₃ | H | H | " | —NH— | 164 (hydrochloride monohydrate) |
| 3-CH₃ | H | H | " | —OCH₂— | 104 (hydrochloride monohydrate) |
| 3-CH₃ | H | H | " | —(CH₂)₂— | 107 (formate) |
| 2-Cl | H | H | " | " | 85 (formate) |
| 2-allyloxy | H | H | " | —NH— | 154 (maleate) |
| 2-allyloxy | H | H | " | —OCH₂— | 183 (sulfate) |
| " | H | H | " | —(CH₂)₂— | 108 (p-aminobenzoate) |
| H | 2,3-CH=CH—CH=CH— | | (CH₃)₂C—(CH₂)₃ | —NH— | 134 (succinate) |
| 2-allyl | H | H | (CH₃)₂C—(CH₂)₂— | " | 162 (maleate) |
| " | H | H | (CH₃)₂C—(CH₂)₃— | —OCH₂— | 181 (p-aminobenzoate) |
| 2-CH₃ | H | H | (CH₃)₂C—(CH₂)₂ | —NH— | 187 (maleate) |
| 2-CH₃ | H | H | (CH₃)₂C—(CH₂)₃— | " | 134 (p-aminobenzoate) |
| 2-CH₃ | H | H | (CH₃)₂C—(CH₂)₂— | —OCH₂— | 157 (p-aminobenzoate) |
| 2-CH₃ | H | H | (CH₃)₂C—(CH₂)₂— | —(CH₂)₂— | 143 (p-aminobenzoate) |
| 2-n-propyl | H | H | " | —NH— | 165 (maleate) |
| 2-n-propoxy | H | H | " | —OCH₂— | 186 (sulfate) |
| 4-OCH₃ | H | H | " | —NH | 193 (maleate) |
| " | H | H | " | —OCH₂— | 159 (p-aminobenzoate) |
| 2-CN | H | H | " | —NH— | 167 (maleate) |

TABLE II

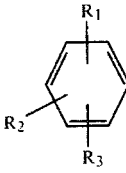

| $R_1$ | $R_2$ | $R_3$ | D | $R_{10}$ | $R_{11}$ | m.p. °C. (salt) |
|---|---|---|---|---|---|---|
| 2-Cl | H | H | $(CH_3)_2C-(CH_2)_2-$ | H | H | 185 (hydrochloride) |
| H | 2,3-CH=CH—CH=CH— | | " | H | H | 228 (hydrochloride) |
| 3-CH$_3$ | H | H | " | H | H | 150 (hydrochloride) |
| 2-allyloxy | H | H | " | H | H | 222 (sulfate) |
| 2-Cl | H | H | " | 2-OCH$_3$ | 4-OCH$_3$ | 183 (sulfate) |
| 2-Cl | H | H | $-(CH_2)_3-$ | H | H | 78 (base), 152 (hydrochloride) |
| 2-allyl | H | H | $(CH_3)_2C(CH_2)_2-$ | H | H | 118 (formate) |
| 2-CH$_3$ | H | H | " | H | H | 181 (hydrochloride) |
| 2-Cl | H | H | " | H | 3-CF$_3$ | 133 (formate) |
| 2-n-propyl | H | H | " | H | H | 110 (formate) |
| 2-n-propoxy | H | H | " | H | H | 226 (sulfate) |
| 2-CN | H | H | " | H | H | 186 (hydrochloride) |

EXAMPLE 2

1-o-Tolyloxy-3-[1-methyl-2-(benzimidazolone-(2)-yl)-ethylamino]-propanol-(2) by method B 750 mgm of platinum oxide were added to a solution of 5.8 gm of 3-acetonyl-benzimidazolone-(2) and 5.06 gm of 1-(2-methyl-phenoxy)-3-amino-propanol-(2) in 120 ml of methanol, and the mixture was hydrogenated until 1 equivalent of hydrogen had been absorbed. After working up the hydrogenation reaction mixture in conventional manner, the compound named in the heading, which had a melting point of 160° C., was obtained.

EXAMPLE 3

1-(2,4-dichloro-phenoxy)-3-[1,1-dimethyl-2-(3-phenylimidazolidinon-(2)-yl)-ethyl-amino-1]-propanol-2 by method A 4.25 gm (0.015 mol) of 1,1-dimethyl-2-(3-phenylimidazolidinony)-ethyl-amine were dissolved in 30 ml of ethanol, and the solution was combined with a solution of 3.3 gm (0.015 mol) of 1-(2,5-dichloro-phenoxy)-2,3-epoxypropane. After the mixture had been refluxed for one hour, the solvent is distilled off in vacuo. The residue was purified by column-chromatography on silicagel. After evaporation of the uniform fractions an oily residue was left behind which was dissolved in ethyl acetate, and the solution was washed twice with water and dried over MgSO$_4$. After distilling off the ethyl acetate 3.2 gm of the free base product was obtained. The base was dissolved in ether, the solution was filtered and caused to crystallize in the cold. The colorless crystallizate was collected by suction filtration and dried, yielding 1.7 gm of the base, m.p. 106°–109° C.

After processing the remaining fractions, an additional 1.9 gm of the pure base were obtained.

Using a procedure analogous to that described in Example 3, the following compounds of the indicated formula were also prepared by refluxing the corresponding 1-phenoxy-2,3-epoxypropane with [1,1-dimethyl-2-(3-phenyl-imidazolidinon-(2)-yl]-amine in ethanol.

TABLE III

| $R_1$ | $R_2$ | m.p. °C. (salt) |
|---|---|---|
| 2-CN | H | 117–118 |
| 2-Br | H | 106–109 |
| 3-CH$_3$ | H | 112–115 |
| 2-CH$_2$—CH=CH$_2$ | H | 85–87 |
| 2-Cl | 6-Cl | 98–100 |
| 2-Cl | 5-CH$_3$ | 01 |
| 2-Cl | H | 96–101 |
| 2-O—CH$_2$—CH=CH$_2$ | H | 134–136 (oxalate) |
| 2-CH$_3$ | 6-CH$_3$ | 73–76 |
| 3-OCH$_3$ | H | 184–186 (oxalate) |
| 4-COC$_2$H$_5$ | H | 138–139 |
| 3-CH$_3$ | 5-CH$_3$ | 177–180 (oxalate) |

EXAMPLE 4

1-(2-Propargyloxy-phenoxy)-3-[1,1-dimethyl-3-(3-phenyl-imidazolidinoxyl)-propylamino-1]-propanol-2 oxalate by method A 4.8 gm (0.017 mol) of 1,1-dimethyl-3-(3-phenylimidazolidinonyl)-propyl-amine hydrochloride were dissolved in 20 ml of methanol, 8.5 gm (0.017 mol) of 2 N NaOH were added, and the mixture was combined with a solution of 3.46 gm (0.017 mol) of 1-(2-propargyloxy-phenoxy)-2,3-epoxypropane in 20 ml of methanol. The resulting mixture was refluxed for one hour, and then the solvent was distilled off. The residue is taken up in ether, the solution was washed with water, separated and dried over Na$_2$SO$_4$. After distilling off the ether, the residue was purified on a silicagel column. The combined uniform fractions were evaporated. The residue was dissolved in ethyl acetate, the solution was washed with water and dried, and then the ethyl acetate was distilled off. The basic residue was dissolved in acetone, and a solution of 3 gm of oxalic acid in acetone was added. After addition of ether the colorless oxalate crystallized out. It was recrystallized once more from a mixture of acetonitrile, ethanol and methanol by addition of ether. The colorless crystallizate (1.6 gm) had a melting point of 207°–209° C. Upon evaporation of the mother liquor, additional oxalate was obtained which, after recrystallization from methanol/ether, had a melting point of 205°–207° C. Total yield of oxalate: 1.5 gm. The thin-layer chromatogram of both fractions was uniform.

Using a procedure analogous to that described in Example 4, the following additional compounds of the indicated formula were prepared from the corresponding 1-phenoxy-2,3-epoxypropane and [1,1-dimethyl-3-(3-phenyl-imidazolidinonyl)-propyl]-amine . HCl in alkaline methanol.

TABLE IV

| R₁ | R₂ | m.p. °C. (salt) |
|---|---|---|
| 2-NO₂ | H | 84–86 |
| 2-Cl | 6-Cl | 84–86 |
| 2-Br | H | 104–107 |
| 2-Cl | 5-CH₃ | 76–78 |
| 3-CH₃ | 4-CH₃ | 102–104 |
| 3,4-(CH₂)₃— | | 97–99 |
| 3-CO—C₂H₅ | H | 147–150 |
| 3-CH₃ | 5-CH₃ | 84–86 |
| 2-O—CH₂—C≡CH | H | 207–208 (oxalate) |
| 2-Cl | 4-Cl | 159–163 (hydrochloride) |
| 4-OCH₃ | H | 97–99 |
| 3-OCH₃ | H | 83–85 |
| 3-CF₃ | H | 119–121 |

EXAMPLE 5

1-(4-Hydroxy-phenoxy)-3-[1,1-dimethyl-3-(3-phenyl-imidazolidinonyl)-propylamino-1]-propanol-2 oxalate by method O 2.5 gm of 1-(4-methoxy-phenoxy)-3-[1,1-dimethyl-3-(3-phenyl-imidazolidinonyl)-propylamino-1]-propanol-3- were heated in 15 ml of HBr for 100 hours at 100° C. Then, the HBr was distilled off in vacuo, and the residue was treated with water. After distilling off the water, the residue was made alkaline with NH₄OH, extracted with ethyl acetate, the organic phase was dried, and the solvent was evaporated in vacuo. The residue was dissolved in acetone, and the solution was added to a solution of 3 gm of oxalic acid in acetone. After addition of ether the oxalate crystallized out, which was isolated, dried and recrystallized from ethanol, whereupon it had a melting point of 198°–200° C. Yield: 200 mgm.

EXAMPLE 6

1-(4-Methoxy-phenoxy)-3-[2-(3-phenyl-imidazolidinonyl)-ethylamino-1]-propanol-2 by method D A mixture of 2.8 gm (0.0122 mol) of 1-(2-chloroethyl)-3-phenyl-imidazolidinone-2, 2.4 gm (0.0122 mol) of 1-(4-methoxy-phenoxy)-3-amino-2-propanol, 15 ml of diglyme (diethyleneglycol-dimethylether) and 1.3 gm (0.0122 mol) of sodium carbonate was heated for two hours at 150°–160° C., while stirring. After distilling off the solvent, the residue was treated with ethyl acetate, washed with NaOH and H₂O and allowed to stand overnight. The separating crystalline substance was recrystallized from ethyl acetate. The colorless crystalline compound melted at 108° to 110° C. Yield: 500 mgm.

By processing the mother liquor, another 200 mgm of the pure product, m.p. 107° to 110° C., were obtained. The thin-layer chromatogram of both fractions was uniform.

Using a procedure analogous to that described in Example 6, the following additional compounds of the indicated formula were prepared from the corresponding 1-phenoxy-3-amino-propanol-(2) and 1-(2-chloroethyl)-3-phenyl-imidazolidinone-(2) in an alkaline diglyme solution:

TABLE V

| R₁ | R₂ | R₄ | m.p. °C. (salt) |
|---|---|---|---|
| 3-OCH₃ | H | CH₃ | 130–134 (hydrochloride) |
| 4-CN | H | CH₃ | 102–104 (hydrochloride) |
| 4-Cl | H | CH₃ | 137–140 (hydrochloride) |
| 3-CH₃ | 5-CH₃ | H | 199–201 (hydrochloride) |
| 3-CH₃ | H | H | 92–95 |

Using a procedure analogous to that described in Example 5, the following compounds of the formula shown in Table V were prepared by hydrolizing the corresponding 3- or 4-methoxy-phenoxy compound with HBr at 100° C.

TABLE VI

| R₁ | R₂ | R₄ | m.p. °C. |
|---|---|---|---|
| 4-OH | H | CH₃ | 150–155 |
| 3-OH | H | CH₃ | viscous |

EXAMPLE 7

1-(2-Cyano-phenoxy)-[3-(3-phenyl-imidazolidinonyl)-propylamino-1]-propanol-2 by method A 0.875 gm (0.005 mol) of 1-(2-cyano-phenoxy)-2,3-epoxypropane and 1.3 gm (0.005 mol) of N-[1-aminopropyl-(3)]-3-phenyl-imidazolidinone-2 were dissolved in 10 ml of ethanol, and the solution was refluxed for 1 hour after addition of 0.75 ml of triethylamine. Afterwards 2.5 ml of 1 N NaOH were added. The solvent was distilled off in vacuo, the residue was admixed with water, and the mixture was extracted with ethyl acetate.

The organic phase was washed, dried and evaporated. The residue was dissolved in ethyl acetate and caused to crystallizate out by cooling. The colorless crystallizate melted at 105° to 108° C. Yield: 800 gm; thin-layer chromatogram uniform.

Using a procedure analogous to that described in Example 7, the following compounds of the indicated formula were also prepared by refluxing the corresponding 1-phenoxy-2,3-epoxypropane with N-(1-amino-propyl-3)-3-phenyl-imidazolidinone-2 in ethanol:

TABLE VI $$R_2 \underset{}{\overset{R_1}{\bigcirc}} -OCH_2-CHOH-CH_2-NH-(CH_2)_3-N\underset{\underset{O}{\|}}{\overset{}{\bigvee}}N-\bigcirc$$

| $R_1$ | $R_2$ | m.p. °C. |
|---|---|---|
| 2-Cl | 5-CH$_3$ | 112–114 |
| 2-Cl | 4-Cl | 119–121 |
| 2-Cl | 6-Cl | 93–95 |
| 2-Br | H | 107–110 |
| 2-CH$_2$—CH=CH$_2$ | H | 114–116 |
| 3-OCH$_3$ | H | 86–88 |
| 4-CO—CH$_3$ | H | 129–131 |
| 2,3-(—CH=CH—)$_2$ | | 84–87 |
| 2-CH$_3$ | 6-CH$_3$ | 102–104 |
| 3-CH$_3$ | H | 94–97 |
| 2-O—CH$_2$—CH=CH$_2$ | H | 108–110 |
| 3-CH$_3$ | 4-CH$_3$ | 78–79 |
| 3,4-(CH$_2$)$_3$ | | 101–103 |
| 4-Cl | H | 128–131 |
| 3-CF$_3$ | H | 105–107 |
| 2-CO—CH$_3$ | H | 85–88 |
| 3-CH$_3$ | 5-CH$_3$ | 103–104 |
| 2-NO$_2$ | H | 102–104 |

EXAMPLE 8

1-(2-Cyano-phenoxy)-3-(1,1-dimethyl-4-N-benzimidazolonyl-butyl-amino-1)-propanol-2 by method A 1.75 gm (0.01 mol) of 1-(2-cyano-phenoxy)-2,3-epoxypropane and 2.16 gm (0.008 mol) of N-(1,1-dimethyl-1-aminobutyl)-benzimidazolone-(2) were dissolved in 80 ml of ethanol, 8 ml of 1 N NaOH were added, and the mixture was heated at its boiling point for 1 hour, while stirring. Afterwards the ethanol was distilled off, the residue was stirred with water and extracted with ethyl acetate. After drying the organic phase, the ethyl acetate was distilled off, and the residue was purified on a silicagel column, whereby 2.5 gm of pure product was obtained. The thin-layer chromatogram is uniform. The oily substance does not crystallize, neither as the base nor as a salt.

1-(2-Bromo-phenoxy)-3-(1,1-dimethyl-4-N-benzimidazolonyl-butyl-amino-1)-propanol-2 was prepared in the same way from 1-(2-bromo-phenoxy)-2,3-epoxypropane and N-(1,1-dimethyl-1-aminobutyl)-benzimidazolone-(2) in ethanol NaOH at reflux temperature.

EXAMPLE 9

1-(3-Methoxy-phenoxy)-3-(1,1-dimethyl-3-(N-benzimidazolonyl-)propylamino-1-)propanol-2 maleate by method A 4 gm (0.022 mol) of 1-(3-methoxy-phenoxy)-2,3-epoxypropane were dissolved in 50 ml of methanol, and a solution of 4.4 gm (0.02 mol) of N-(1,1-dimethyl-1-aminopropyl)-benzimidazolone in 50 ml of methanol was added. After having refluxed the mixture for 1.5 hrs., the solvent was distilled off, and the residue was purified on a silicagel column. After distilling off the mixture of solvents, the uniform fractions yielded 7 gm of residue, which was dissolved in acetone and stirred into a solution of maleic acid in acetone. After addition of ether, the maleate crystallized out. It was separated and recrystallized from methanol by addition of ether. Yield: 6 gm; m.p. 167°–169° C. The thin-layer chromatogram was uniform.

Using a procedure analogous to that described in Example 9, the following additional compounds of the indicated formula were prepared by refluxing the corresponding 1-phenoxy-2,3-epoxypropane with N-(1,1-dimethyl-1-aminopropyl)-benzimidazolone-(2) in methanol:

TABLE VII $$R_2\underset{}{\overset{R_1}{\bigcirc}}-O-CH_2-\underset{OH}{\overset{}{CH}}-CH_2-HN-\underset{CH_3}{\overset{CH_3}{C}}-CH_2-CH_2-N\underset{\underset{O}{\|}}{\overset{}{\bigvee}}NH$$

| $R_1$ | $R_2$ | m.p. °C. (maleate) |
|---|---|---|
| 2-Cl | 6-Cl | 168–170 |
| 2-Br | H | 160–162 |
| 2-Cl | 5-CH$_3$ | 174–175 |
| 2-CH$_3$ | 6-CH$_3$ | 183–184 |
| 3-CF$_3$ | H | 185–187 |
| 4-CO—C$_2$H$_5$ | H | 195–197 |
| 2-CO—CH$_3$ | 4-NHCOC$_3$H$_7$ | 145–147 |
| 4-NO$_2$ | H | 213–215 |
| 3-CH$_3$ | 5-CH$_3$ | 136–139 (Base) |
| 2-O—CH$_2$—C≡CH | H | 154–157 |
| 2-Cl | 4-Cl | 191–193 |

Using a procedure analogous to that described in Example 5, the following compounds of the formula shown in Table VIII were prepared by hydrolysis of the corresponding 3- or 4-methoxy-phenoxy compound with HBr:

| $R_1$ | $R_2$ | m.p. °C. (maleate) |
|---|---|---|
| 4-OH | H | 121–125 |
| 3-OH | H | 156–159 |

EXAMPLE 10

1-(2-Propargyloxy-phenoxy)-3-(1,1-dimethyl-2-N-benzimidazolonylethylamino-1)-propanol-2-hydrochloride by method A 2.25 gm (0.011 mol) of 1-(2-propargyloxy-phenoxy)-2,3-epoxy-propane were dissolved in 50 ml of methanol, and a methanolic solution of 2 gm (0.01 mol) of N-(1,1-dimethyl-1-aminoethyl)-benzimidazolone was added. After refluxing for one hour, the solvent was distilled off, the residue was dissolved in ethanol, and ether was added. The hydrochloride separated out as colorless crystals, which were separated and recrystallized once more from methanol by addition of ether. Yield: 2,3 gm; m.p. 203°–205° C. The thin-layer chromatogram was uniform.

Using a procedure analogous to that described in Example 10, the following compounds of the indicated formula were prepared by refluxing the corresponding 1-phenoxy-2,3-epoxypropane and N-(1,1-dimethyl-1-aminoethyl)-benzimidazolone-(2) in methanol.

TABLE IX

R2—[phenyl with R1]—O—CH2—CH(OH)—CH2—HN—C(CH3)(CH3)—CH2—N(benzimidazolonyl)

| R1 | R2 | M.p. °C. |
|---|---|---|
| 2-CN | H | 195-197 (hydrochloride) |
| 2-Cl | 6-Cl | 242-244 (hydrochloride) |
| 2-Br | H | 201-203 (hydrochloride) |
| 2-CH2—CH=CH2 | H | 243-245 (hydrochloride) |
| 2-Cl | 5-CH3 | 210-212 (hydrochloride) |
| 4-OCH3 | H | 214-216 (hydrochloride) |
| 3-OCH3 | H | 191-194 (hydrochloride) |
| 2-O—CH2—CH=CH2 | H | 179-181 (hydrochloride) |
| 2-Cl | 4-Cl | 239-241 (hydrochloride) |
| 2-Cl | 6-Cl | 132-136 |
| 2-CN | H | 90-94 |
| 2-Br | H | 128-130 |
| 2-O—CH2—CH—CH2 | H | 78-81 |
| 3-CH3 | H | 104-105 |
| 3-CF3 | H | 139-140 |
| 2-CO—CH3 | 4-NHCOC3H7 | 166-169 |
| 4-OCH3 | H | 117-120 |
| 4-COC2H5 | H | 143-146 |
| 2,3-(—CH=CH—CH=CH)— | | 150-154 |
| 3-OCH3 | H | viscous |
| 2-Cl | 4-Cl | 140-143 |
| 2-O—CH2—C≡CH | H | 101-103 |

Using a procedure analogous to that described in Example 5, the following additional compounds of the formula shown in Table IX were prepared by hydrolysis of the corresponding 3- or 4-methoxy-phenoxy compound with HBr at 100° C.:

TABLE X

| R1 | R2 | m.p. °C. (hydrobromide) |
|---|---|---|
| 4-OH | H | 248-251 |
| 3-OH | H | 230-232 |

EXAMPLE 11

1-(m-Tolyloxy)-3-(N-benzimidazolonyl-3-propyl-amino-1)-propanol-3 by method A 3.28 gm (0.02 mol) of 1-(m-tolyloxy)-2,3-epoxypropane and 3.8 gm (0.02 mol) of 3-benzimidazolonyl-propylamine-(1) were dissolved in 100 ml of ethanol, and the solution was refluxed for 30 minutes. After distilling off the solvent, the residue was fractionated on a silicagel column. After the mixture of solvents had been distilled off, the uniform fractions yielded a residue which was recrystallized from ethyl acetate by addition of petroleum ether. After isolating and drying, 2.8 gm of base were obtained. M.p. 133°-135° C. The thin-layer chromatogram was uniform.

Analogous to Example 11, the compounds of the indicated formula listed in the following table were prepared by refluxing the corresponding 1-phenoxy-2,3-eposypropane and 3-benzimidazolonyl-propyla-mine-(1) in ethanol:

TABLE XI

R2—[phenyl with R1]—O—CH2—CH(OH)—CH2—NH—(CH2)3—N(benzimidazolonyl)

| R1 | R2 | m.p. °C. |
|---|---|---|
| 2-CN | H | 158-159 (oxalate) |
| 2-Br | H | 137-140 (hydrochloride) |
| 2-Cl | 5-CH3 | 178-180 (hydrochloride) |
| 2-Cl | H | 140-143 (hydrochloride) |
| 4-OCH3 | H | 131-132 (Base) |
| 2-O—CH2—CH=CH2 | H | 101-104 (Base) |
| 2-Cl | 6-Cl | 154-158 (Base) |
| 4-NH—CO—C3H7 | 6-CO—CH3 | 140-143 (Base) |
| 4-CO—CH3 | H | 122-125 (Base) |
| 2-CH2—CH=CH2 | H | 97-99 (Base) |

EXAMPLE 12

1-(2-Cyano-phenoxy)-3-(1,1,4,4-tetramethyl-4-N-benzimidazol-onyl-butylamino-1)-propanol-2 oxalate by method A 2.61 gm (0.01 mol) of N-(1-amino-1,1,4,4-tetramethyl-butyl)-benzimidazolone and 3.5 gm (0.02 mol) of 1-(2-cyanophenoxy)-2,3-epoxypropane were dissolved in 100 ml of ethanol, and the solution was refluxed for one hour. After having distilled off the ethanol, the residue was admixed with water, NaOH was added, the mixture was extracted with ethyl acetate, and the organic phase was washed with water and dried over sodium sulfate. The ethyl acetate was distilled off, and the residue was purified on a silicagel column. The combined uniform fractions were evaporated, the residue was dissolved in acetonitrile, and a solution of 1.5 gm of oxalic acid in acetonitrile was added. Upon addition of ether, the colorless oxalate crystallized out, which was recrystallized from acetonitrile by addition of ether. Yield: 1.7 gm; m.p. 107°-109° C. The thin-layer chromatogram was uniform.

Analogous to the procedure of Example 12, the following compounds of the indicated formula were prepared by refluxing the corresponding 1-phenoxy-2,3-epoxypropane with N-(1-amino-1,1,4,4-tetramethyl-butyl)-benzimidazolone-(2) in ethanol:

TABLE XII

R2—[phenyl with R1]—O—CH2—CH(OH)—CH2—NH—C(CH3)(CH3)—(CH2)2—C(CH3)(CH3)—N(benzimidazolonyl)

| R1 | R2 | m.p. °C. (Base) |
|---|---|---|
| 2-Cl | 4-Cl | 99-103 |
| 2-Cl | 5-CH3 | 100-103 |
| 2-O—CH2—CH=CH2 | H | 120-125 |
| 2-CH2—CH=CH2 | H | 147-148 |
| 2-Cl | 6-Cl | 113-115 |
| 3-OCH3 | H | 128-131 |
| 4-CO—CH3 | H | 131-133 |
| 2-Br | H | 100-102 |
| 2-CH3 | 6-CH3 | 118-122 |
| 4-CH3 | H | 135-137 |
| 2-OCH3 | H | 91-93 |
| 2-CH3 | 4-CH5 | 109-111 |
| 4-OCH3 | H | 108-111 |
| 2-O—CH2—C≡CH | H | 109-110 |
| 3-CH5 | H | 118-110 |

TABLE XII-continued

[Structure: R₂—[phenyl with R₁]—O—CH₂—CH(OH)—CH₂—NH—C(CH₃)(CH₃)—(CH₂)₂—C(CH₃)(CH₃)—N with fused benzene ring, carbonyl, NH]

| R₁ | R₂ | m.p. °C. (Base) |
|---|---|---|
| 2,3-(—CH=CH—)₂— | | 90–92 |

EXAMPLE 13

1-(2,4-Dichloro-phenoxy)-3-[1,1-dimethyl-3-(N-1,2,3,4-tetrahydroquinolonyl)-propyl-amino]-propanol-2 oxalate by method A 4,6 gm of N-(1-amino-1,1-dimethyl-propyl)-1,2,3,4-tetrahydroquinolone-(2) and 6 gm of 1-(2,4-dichloro-phenoxy)-2,3-epoxypropane were dissolved in 100 ml of ethanol, and the solution was refluxed for one hour and was then evaporated. The residue is admixed with water, and the mixture was acidified with HCl and then extracted with ether. The aqueous phase was made alkaline with dilute NaOH, and the precipitated base was taken up in ether. After washing with water, the ethereal phase was dried over Na₂SO₄, separated and evaporated. The residue was purified on a silicagel column, and the combined fractions were evaporated. The residue was dissolved in acetonitrile, the solution was combined with a solution of oxalic acid in acetonitrile, and ether was added, whereby the oxalate precipitated as fine crystals. After recrystallization from ethanol/ether, 3.1 gm of a colorless crystalline substance were obtained, the melting point of which was 144°–145° C. The thin-layer chromatogram was uniform.

Using a procedure analogous to that described in Example 13, the following additional compounds of the indicated formula were prepared by refluxing the corresponding 1-phenoxy-2,3-epoxypropane with N-(1-amino-1,1-dimethyl-propyl)-1,2,3,4-tetrahydroquinolone-(2) in ethanol:

TABLE XIII

[Structure: R₂—[phenyl with R₁]—O—CH₂—CH(OH)—CH₂—NH—C(CH₃)—CH₂—CH₂—N with fused benzene ring, C=O]

| R₁ | R₂ | m.p. °C. (salt) |
|---|---|---|
| 2-Cl | 6-Cl | viscous oil (hydrochloride) |
| 2-Cl | 5-CH₃ | 151–153 (oxalate) |
| 4-Cl | H | 116–117 |
| 2-CH₂—CH=CH₂ | H | 118–120 (maleate) |
| 2-CN | H | 93–97 (hydrochloride) |
| 2-OCH₃ | H | 128–129 (oxalate) |
| 4-OCH₃ | H | 85–86 |
| 2-O—CH₂—C≡CH | H | 82–84 (oxalate) |
| 2-CH₃ | 6-CH₃ | 113–115 (oxalate) |

Analogous to Example 5, the following compounds of the formula shown in Table XIII were prepared by hydrolysis of the corresponding 2- or 4-methoxyphenoxy compounds with HBr at 100° C.:

TABLE IV

| R₁ | R₂ | m.p. °C. (salt) |
|---|---|---|
| 2-OH | H | 199–200 (oxalate) |
| 4-OH | H | 123–124 |

Using a procedure analogous to that described in Example 13, the following additional compounds of the indicated formula were prepared by refluxing the corresponding 1-phenoxy-2,3-epoxypropane with N-(1-benzylamino-propyl)-1,2,3,4-tetrahydroquinolone-(2) in ethanol:

TABLE XV

[Structure: R₂—[phenyl with R₁]—OCH₂—CH(OH)—CH₂—N(R₄)—(CH₂)₃—N with fused benzene ring, C=O]

| R₁ | R₂ | R₄ | m.p. °C. (salt) |
|---|---|---|---|
| 2-Br | H | H | 164–167 (hydrochloride) |
| 2-OCH₃ | H | H | 126–128 (hydrochloride) |
| 3-CH₃ | H | H | 125–126 (hydrochloride) |
| 4-OCH₃ | H | H | 116–117 (hydrochloride) |
| 2-CH₃ | H | H | 148–149 (hydrochloride) |
| 2-OCH₃ | H | —CH₂—C₆H₅ | oil |
| 3-CH₃ | H | —CH₂—C₆H₅ | oil |
| 4-OCH₃ | H | —CH₂—C₆H₅ | oil |
| 3-OCH₃ | H | —CH₂—C₆H₅ | oil |
| 2-CH₃ | H | —CH₂—C₆H₅ | oil |

EXAMPLE 14

1-(3-Methoxy-phenoxy)-3-[3-(N-1,2,3,4-tetrahydroquinolone-2-yl)-propyl-amino]-propanol-2 hydrochloride by method A 6.1 gm of 1-(3-methoxy-phenoxy)-3-[3-(N-1,2,3,4-tetrahydroquinolone-2-yl)-benzylpropylamino]-propanol-2 were dissolved in 50 ml of methanol, and the solution was hydrogenated in the presence of palladium-on-charcoal at 60° C. and 6 atmospheres. After the absorption of hydrogen had ceased, the catalyst was suction-filtered off, the solvent was distilled out of the filtrate, and the residue was purified on a silicagel column. After having distilled off the solvent, the uniform fractions yielded a residue which was dissolved in ethanolic HCl. After addition of ether the colorless hydrochloride crystallized out, which was recrystallized once more from methanol. Yield: 2.7 gm; m.p. 122°–123° C. The thin-layer chromatogram was uniform.

EXAMPLE 15

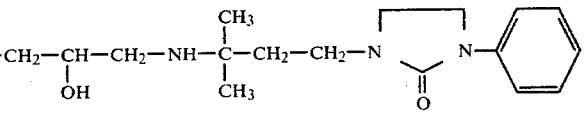

by method E

A solution was prepared from 20 ml of ethanol, 5 ml of water, 1.5 gm of potassium hydroxide and 0.5 gm of the compound of the formula

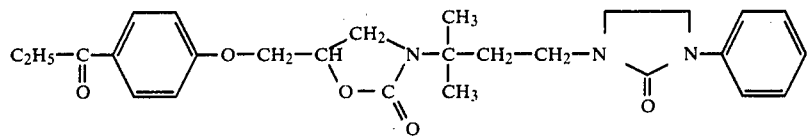

The solution was refluxed for one hour and was then evaporated. The residue was admixed with 40 ml of water, and the mixture was acidified with aqueous 10% HCl and extracted twice with methylene chloride (40 ml). The aqueous phase was made alkaline with aqueous 10% NaOH while cooling on ice, extracted twice with 50 ml each of methylene chloride, and the methylene chloride phase was washed once with 50 ml of water, dried over Na₂SO₄, and evaporated. The residue was recrystallized from isopropanol. M.p. 147°-149° C.

EXAMPLE 16

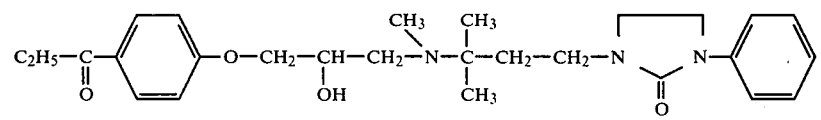

by method A.

A solution was prepared from 1.1 gm (0.0024 mol) of the compound of the formula

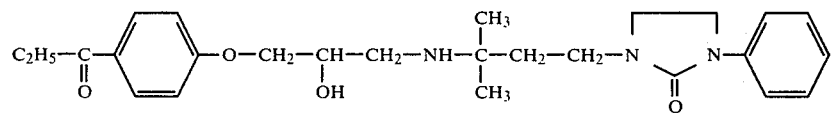

3 ml of formic acid and 6 ml of aqueous 30% formaldehyde, and the solution was refluxed for one hour on a water bath. Carbon dioxide was given off during that time. The reaction mixture was then cooled, diluted with 30 ml of water and extracted twice with 50 ml of ether each. The aqueous phase was made alkaline with aqueous 10% NaOH, then extracted 3 times with 30 ml of ethyl acetate each, and the ethyl acetate phase was washed once with 20 ml of water, dried over Na₂SO₄ and evaporated. The residue was purified on a silicagel column with a solution of 70 ml of ethyl acetate, 30 ml of isopropanol and 2.5 ml of 25% ammonia. The pure product was dissolved in acetonitrile, acidified with ethanolic HCl, precipitated with ether, collected by suction filtration, and recrystallized once from acetonitrile and ether. M.p. 191°-195° C. Thin-layer chromatogram: pure.

EXAMPLE 17

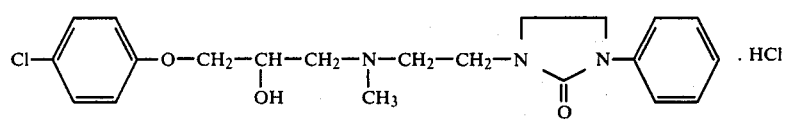

by method F 880 gm (about 0.002 mol) of the compound of the formula

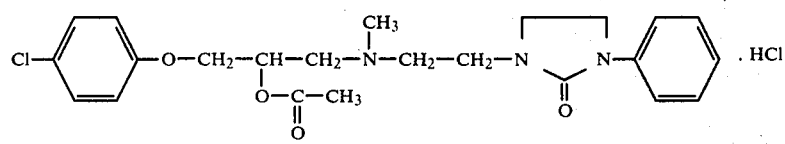

were dissolved in 15 ml of ethanol, a solution of 1 gm of potassium hydroxide in 3 ml of water was added, and the mixture was refluxed for one hour. Thereafter, the solvent was distilled off in vacuo, the residue was admixed with water, and the mixture was extracted twice with ethyl acetate. The ethyl acetate phase was washed with water, dried over Na₂SO₄ filtered and evaporated, and the residue was recrystallized from acetonitrile by addition of ether. M.p. 135°-137° C.

EXAMPLE 18

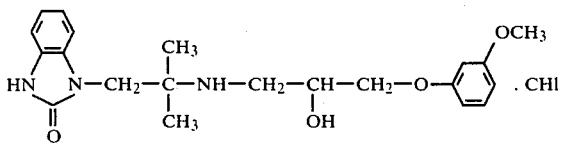

by method C.

0.7 gm (about 0.0025 mol) of the compound of the formula

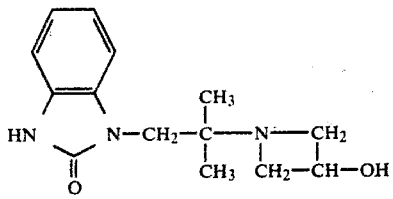

was dissolved in 20 ml of benzyl alcohol, and then 0.4 gm (about 0.003 mol) of 3-methoxy-phenol and 0.1 gm of KOH were added. The mixture was allowed to react for 5 hours on an oil bath at 140° C. Thereafter, the solvent was distilled off in vacuo, the residue was acidified with 1 N HCl and extracted twice with a little ethyl acetate. The ethyl acetate phase was dried over $Na_2SO_4$ and evaporated, and the residue was purified on a silicagel column.

EXAMPLE 19

1-(2-Amino-phenoxy)-3-[3-(3-phenyl-imidazolidinonyl)-propyl-amino-1]-propanol-2 by method N 3 gm of 1-(2-nitro-phenyl)-3-[3-(3-phenyl-imidazolidinonyl)-propyl-amino-1]-propanol-2 were dissolved in 100 ml of methanol, and the solution was hydrogenated in the presence of Raney nickel at room temperature and atmospheric pressure. After the theoretical quantity of hydrogen had been absorbed, the catalyst was suction-filtered off, and the solvent was distilled off in vacuo. The residue was dissolved in acetonitrile, and the solution was acidified with methanolic HCl. The resulting colorless crystallizate was filtered off and dried. Yield: 1.9 gm; m.p. 190°–192° C.; thin-layer chromatogram uniform.

EXAMPLE 20

1-(2-Cyano-phenoxy)-3-[3-(3-phenyl-imidazolidinonyl)-propyl-amino-1]-propanol-2 by method L 876 mgm (0.0015 mol) of 1-(2-amino-phenoxy)-3-[3-(3-phenyl-imidazolidinonyl)-propyl-amino-1]-propanol-2 dihydrochloride were dissolved in 5 ml of water. After addition of 1 ml of concentrated HCl, a solution of 207 mgm of $NaNO_2$ in 25 ml of water was added dropwise at 3° to 5° C. The homogeneous solution was stirred for 60 minutes at 20° C. Then, the solution was added dropwise at 80°–90° C. to a hot mixture of 800 mgm $CuSO_4.H_2O$, 850 mgm of KCN and 5 ml of water, while stirring. After the addition was finished, the mixture was made alkaline with NaOH. Resinous portions were separated, and the aqueous solution was extracted with ethyl acetate. The organic phase was washed with water, dried over $Na_2SO_4$ and evaporated in vacuo. The viscous residue was fractionated on a silicagel column. The uniform fractions were combined, the solvent was distilled off in vacuo, and the residue was recrystallized from ethyl acetate. The colorless crystallizate melted at 103° to 107° C. The thin-layer chromatogram was uniform, and the $R_f$-value was identical to that of the compound obtained in Example 7.

The preparation of the novel intermediates of the formula III is illustrated by the following examples:

EXAMPLE 21

Reaction of 69.6 gm of the compound of the formula

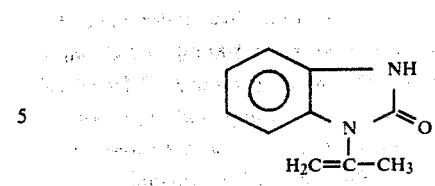

with 55.6 gm of chloroacetone in acetone in the presence of potash and potassium iodide, followed by acid-catalyzed hydrolysis of the intermediate, yielded 32 gm of the compound of the formula

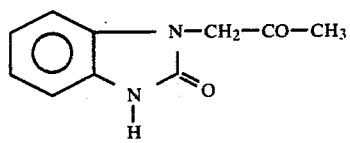

which had a melting point of 182° C. 19 gm of this compound were admixed with 300 ml of methanol and 25 ml of ammonia, and the mixture was hydrogenated at 40°–60° C. and 5 atmospheres in the presence of Raney nickel as a catalyst. The reductive amination yielded 15.6 gm of the hydrochloride, m.p. 267°–270° C., of the formula

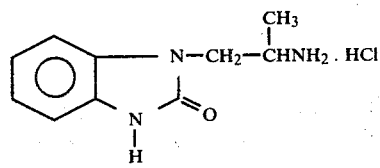

EXAMPLE 22

69.6 gm of the compound of the formula

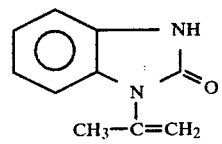

and then 0.44 mol of 3-dibenzylamino-propyl chloride in 300 ml of absolute ethanol were added to a solution of 0.42 mol of sodium in 200 ml of absolute ethanol, and the mixture was refluxed for 6 hours. Thereafter, the pricipitated sodium chloride was separated, and the liquid phase was admixed with 45 ml of concentrated sulfuric acid while stirring and cooling. After three hours, 700 ml of water was added, the ethanol was distilled off, and ammonia was added to the aqueous residue, yielding the compound of the formula

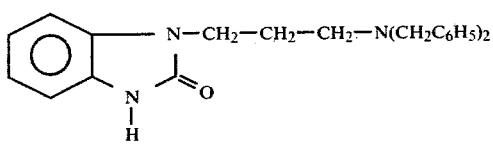

which had a melting point of 146° C. after recrystallization from acetonitrile.

60 gm of this compound were hydrogenated at 60° C. and 5 atmospheres in a mixture of 500 ml of methanol and 200 ml of water and in the presence of 16 ml of concentrated hydrochloric acid and palladium-on-charcoal until 1 equivalent of hydrogen had been absorbed. 88% of theory of the compound of the formula

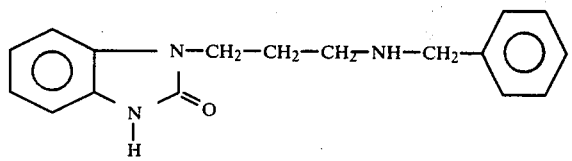

having a melting point of 60° C. was isolated from the reaction mixture.

EXAMPLE 23

A solution of 53.4 gm of the compound of the formula

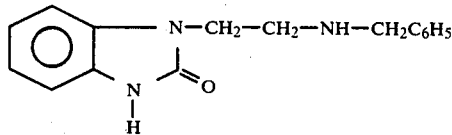

in 420 ml of methanol and 80 ml of water was hydrogenated in the presence of 20 ml of concentrated hydrochloric acid and palladium-on-charcoal at 60° C. and 5 atmospheres until 1 equivalent of hydrogen had been absorbed. 91% of theory of the hydrochloride, m.p. 315° C., of the formula.

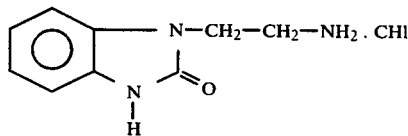

was isolated from the reaction mixture.

EXAMPLE 24

10.1 gm of sodium hydride and 45 gm of N-(3-chloropropyl)-phthalimide were added in an atmosphere of nitrogen to a solution of 31.1 gm of the compound of the formula

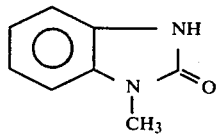

in 150 ml of hexametapol, and the mixture was stirred for 5 hours at 100° C. The crude intermediate of the formula

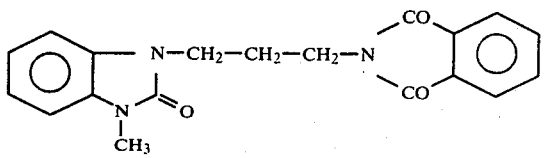

isolated therefrom was refluxed in 1 liter of ethanol with 13 gm of 85% hydrazine hydrate for 90 minutes. Thereafter, the reaction solution was admixed with 21 ml of concentrated hydrochloric acid and 100 ml of water, and the mixture was again heated for 20 minutes. The precipitated phthalic acid hydrazide was separated by suction filtration, and the hydrochloride of the formula

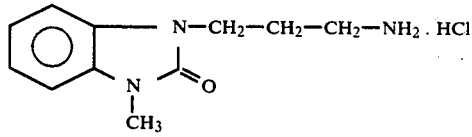

which had a melting point of 195° C. after recrystallization from ethanol, was isolated from the filtrate.

EXAMPLE 25

3.3 gm of 55% sodium hydride were added in an atmosphere of nitrogen to a solution of 9.2 gm of the compound of the formula

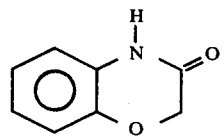

in 40 ml of absolute hexametapol, and after evolution of the calculated amount of hydrogen a solution of 3-benzalamino-propyl chloride (b.p. 140° C. at 12 mm Hg) in 13 ml of hexametapol was added. The resulting mixture was stirred for 5 hours at 100° C., then poured over ice, and the intermediate of the formula

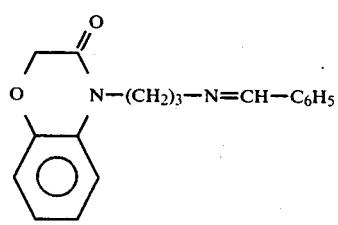

was isolated therefrom by extraction with ether. The intermediate was hydrolized with 2 N HCl without further purification, yielding 67% of theory of the hydrochloride of the formula

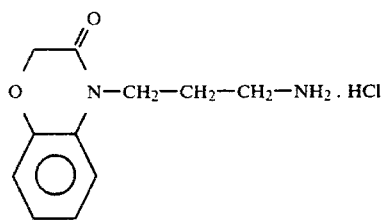

which had a melting point of 152°–155° C.

Analogous to Examples 21 to 25, the following intermediates of the formula III were also prepared:

TABLE XVI

| Formula | m.p. °C. Base | Salt | m.p. °C. Salt |
|---|---|---|---|
| (benzimidazolinone with N–CH₂–CH₂–C(CH₃)₂–NH₂) | 175 | hydrochloride × H₂O | 280 |
| (benzazepinone with N–CH₂–CH₂–CH₂–NH₂) | | hydrochloride | 150 |
| (dihydroquinolinone with N–CH₂–CH₂–C(CH₃)₂–NH₂) | | maleate | 157 |
| (dichloro dihydroquinolinone with N–CH₂–CH₂–CH₂–NH₂) | | hydrochloride | 214–216 |
| (N-methyl benzimidazolinone with N–CH₂–CH₂–C(CH₃)₂–NH₂) | | hydrochloride | 277–279 |
| (benzoxazinone with N–CH₂–CH₂–C(CH₃)₂–NH₂) | | hydrochloride | 237–239 |
| (benzimidazolinone with N–(CH₂)₃–C(CH₃)₂–NH₂) | | hydrochloride | 266–268 |
| (phenyl imidazolidinone with N–CH₂–CH₂–C(CH₃)₂–NH₂) | 76 | hydrochloride × H₂O | 104.5 |
| (benzimidazolinone with N–CH₂–C(CH₃)₂–NH₂) | 135 | hydrochloride | 306 |

TABLE XVI-continued

| Formula | m.p. °C. Base | Salt | m.p. °C. Salt |
|---|---|---|---|
| [2-(3-aminopropyl-methylamino)phenyl]acetamide structure with N—(CH$_2$)$_3$—NH$_2$ | | hydrochloride | 253 |
| 1-(2-chlorophenyl)-3-(3-amino-3-methylbutyl)imidazolidin-2-one | | p-aminobenzoate | 245 |
| 1-(2,3-dimethoxyphenyl)-3-(3-amino-3-methylbutyl)imidazolidin-2-one | | p-aminobenzoate | 225 |
| 1-(3,4-methylenedioxyphenyl)-3-(3-amino-3-methylbutyl)imidazolidin-2-one | | p-aminobenzoate | 233 |
| N-(1-methyl-2-aminoethyl) benzamide derivative | | hydrochloride | 267–270 |
| benzoxazinone with N—(CH$_2$)$_3$—C(CH$_3$)$_2$—NH$_2$ | | maleate | 179 |
| 1-[3-(trifluoromethyl)phenyl]-3-(3-amino-3-methylbutyl)imidazolidin-2-one | 81 | hydrochloride | 246 |
| 1-phenyl-3-[2-(benzylamino)ethyl]imidazolidin-2-one | | hydrochloride | 246 |

EXAMPLE 26

A solution of 174 gm of the compound of the formula

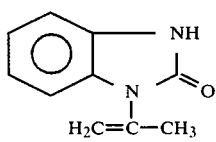

in 700 ml of absolute hexametapol was admixed with 48 gm of a 55% NaH suspension and, after the evolution of hydrogen had ceased, a solution of 341 gm of the compound of the formula

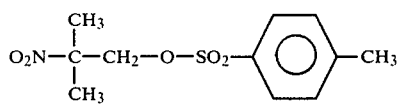

(m.p. 76° CO in 450 ml of hexametapol was added. The resulting solution was stirred for 5 hours at 100° C., then poured on ice, extracted with ether and, after evaporation of the ethereal extract, the residue was dissolved in 3 liters of ethanol, and the solution was admixed with 300 ml of 5 N sulfuric acid. The next day, the compound of the formula

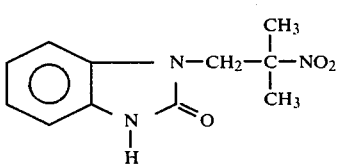

m.p. 198° C., was isolated from the reaction mixture with a yield of 61% of theory. 58.75 gm of this compound were dissolved in 1700 ml of methanol, and after addition of Raney nickel the mixture was hydrogenated at 5 atmospheres and 40°–60° C. The compound of the formula

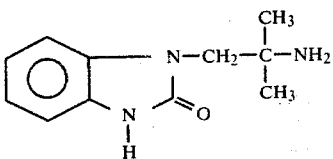

m.p. 135° C., was isolated from the reaction mixture with a yield of 92% of theory.

The preparation of the novel intermediates of the formula VIII is illustrated by the following example:

EXAMPLE 27

N-(1,1-dimethyl-2-benzimidazolonyl-ethyl)-azetidinol 3.1 gm of N-(1-amino-2,2-dimethyl-ethyl)-benzimidazolone were dissolved in 30 ml of acetonitrile, and 1.4 gm of epichlorohydrin were added. The mixture was refluxed for 6 hours. After cooling, it was evaporated in vacuo. The residue was digested with water and extracted with ethyl acetate. The aqueous phase was made alkaline with NaOH and was then extracted with ethyl acetate. The organic phase was dried, and the ethyl acetate was distilled off, leaving 1.4 gm of N-(1,1-dimethyl-2-benzimidazolonyl-(ethyl)-azetidinol.

The preparation of the novel intermediates of the formula X is illustrated by the following examples:

EXAMPLE 28

1-(2-Chloro-ethyl)-2-(4-chloro-phenyl)-imidazolidinone 22.4 gm (0.15 mol) of N-(2-chloro-ethyl)-oxazolidinone-2 were heated with 23 gm (0.15 mol) of 4-chlorophenylisocyanate in the presence of lithium chloride for 5 hours at 160°–180° C. The cooled crystal slurry was recrystallized from ethanol. Yield: 26 gm; m.p. 105°–107° C.

EXAMPLE 29

N-(2-chloro-propyl)-benzimidazolone 13.2 gm of N-(2-hydroxy-propyl)-benzimidazolone were issolved in 150 ml of dioxane, and after addition of 8 ml of SOCl2 the mixture was refluxed for one hour. After evaporation in vacuo, the residue was dissolved in ethyl acetate, and the solution was washed with a sodium bicarbonate solution and water, and dried over Na2SO4. After distilling off the solvent, 13.4 gm of N-(2-chloro-propyl)-benzimidazolone were obtained.

The compounds of the present invention, that is, those embraced by formula I and their non-toxic, pharmacologically acceptable acid addition salts, have useful pharmacodynamic properties. More particularly, they exhibit α- and β-adrenolytic activities in warm-blooded animals such as rats, guinea pigs, rabbits and cats. Therefore, the compounds of the present invention are useful in several therapeutic areas.

Thus, they may be used, for example, for the treatment or prophylaxis of diseases of the coronaries and for the treatment of cardiacarrhythmia, especially tachycardia. Their action is stronger than that of known commercial products such as propranolol or toliprolol. Of extreme therapeutic significance is their usefulness for the treatment of forms of hypertonia. Compared with known α-blockers such as, for example, the phentolamine, they have the advantage of significantly lesser or missing tachycardiac side-effects. A third area of use is as antidepressants, i.e. the treatment of disorders resulting from depression.

An extremely useful compound which is effective as an α- as well as β-adrenolytically active blood-pressure decreasing agent, is 1-(α-naphthoxy)-3-[(1,1-dimethyl-3-benzimidazolidinone-2-yl-propyl)amino]-propanol-2 in the form of an acid addition salt, for example, as its hydrochloride. In tests on genetically hypertonic rats this compound shows, when administered once i.p. and orally as well as several times orally, a decrease of the blood pressure and bradycardia lasting for 24 hours (doses of 10 and 30 mgm/kg). In anesthetized rabbits and cats, blood pressure decrease and bradycardia show after intravenously administered doses of 3 mgm/kg. The α-adrenolytic action is by decimal powers weaker than that of phentolamine (isolated seminal vesicle of the rate). The β-adrenolytic action is 3 to 4 times greater than that of propranolol.

A β-adrenolytically extremely active compound (approximately 10 to 12 times stronger than propranolol) with a clear bradycardiac action p.o. is also 1-(2-bromophenoxy)-3-(N-benzimidazolonyl-3-propylamino)-propanol-(2) in the form of its acid addition salts, for example as its hydrochloride (the test was carried out on guinea-pigs under urethane anesthesia).

The following compounds also exhibit outstanding pharmacological properties in the activity areas mentioned above:

(a) Compounds with excellent β-adrenolysis

1-[3,3-dimethyl-3-(3-o-chloro-phenoxy-2-hydroxy-propyl)-propylamino]-3-phenyl-imidazolidinone-2

1-(2-chloro-phenoxy)-3-[1,1-dimethyl-3-benzimidazolidinone-2-yl-propyl)amino]-propanol-(2)

1-[1,1-dimethyl-3-(3-phenyl-imidazolidinone-2-yl)propyl-amino]-3-(2-methyl-phenoxy)-propanol-(2)

1-(2-allyl-phenoxy)-3-(N-benzimidazolonyl-3-propylamino)-propanol-(2)

1-(3-methyl-phenoxy)-3-(N-benzimidazolonyl-3-propylamino)-propanol-(2)

1-(3-methoxy-phenoxy)-3-[1,1-dimethyl-3-(3-phenyl-imidazolidinonyl)propylamino-1]-propanol-(2)

1-(2-propargyloxy-phenoxy)-3-[1,1-dimethyl-3-(3-phenyl-imidazolidinonyl)propylamino-1]propanol-(2)

1-(2-acetyl-4-aminobutyryl-phenoxy)-3-(3-N-benzimidazolonyl-1,1-dimethyl-1-propylamino)-propanol(2)

1-(2-chloro-5-methyl-phenoxy)-3-(3-N-benzimidazolonyl-1,1-dimethyl-1-propylamino)-propanol-(2)

(b) Compounds with excellent hypotensive and/or bradycardiac action 1-(2-chloro-phenoxy)-3-[1,1-dimethyl-3-benzimidazolidinone-2-yl-propyl)amino]-propanol-(2)

1-[1,1-dimethyl-3-(3,4-dihydro-1,4-2H-benzoxaz-3-onyl)-propylamino]-propanol-(2)

1-[1,1-dimethyl-3-(3-phenyl-imidazolidinone-2-yl)propylamino]-3-(3-methyl-phenoxy)-propanol-(2)

1-(3-methyl-phenoxy)-3-[3-(N-1,2,3,4-tetrahydroquinolone(2)-1,1-dimethyl-propylamino]-propanol-(2)

1-(2-n-propyl-phenoxy)-3-[1,1-dimethyl-3-(3-phenyl-imidazolidinonyl)-propylamino]-propanol-(2)

1-(4-methoxy-phenoxy)-3-[1,1-dimethyl-3-(3-phenyl-imidazolonyl)-propylamino-1]-propanol-(2)

1-(2-allyl-phenoxy)-3-[(1,1-dimethyl)-2-(3-phenyl-imidazolidinonyl)ethylamino-1]-propanol-(2)

1-(3-trifluoromethyl-phenoxy)-3-[1,1-dimethyl-2-(3-phenylimidazolidinonyl)ethylamino-1]-propanol-(2)

1-(indanyloxy)-3-[1,1-dimethyl-3-(3-phenyl-imidazolidinonyl)propylamino-1]propanol-(2)

1-(3,5-dimethylphenoxy)-3-[1,1-dimethyl-3-(3-phenyl-imidazolidinonyl)-propylamino-1]-propanol-(2)

1-(2-propargyloxy-phenoxy)-3-[1,1-dimethyl-3-(3-phenyl-imidazolidinonyl)-propylamino-1]-propanol-(2)

1-(3-methoxy-phenoxy)-3-[1,1-dimethyl-3-(3-phenyl-imidazolidinonyl)-propylamino-1]-propanol-(2)

1-(3,5-dimethyl-phenoxy)-3-[2-(3-phenyl-imidazolidinonyl)-ethylamino-1]-propanol-(2)

1-(3-methyl-phenoxy)-3-[2-(3-phenyl-imidazolidinonyl)-ethylamino-1]-propanol-(2)

1-(3,5-dimethyl-phenoxy)-3-[3-(3-phenyl-imidazolidinonyl)-propylamino-1]-propanol-(2)

1-(2,6-dimethyl-phenoxy)-3-[1,1-dimethyl-3-(N-benzimidazolonyl)-propylamino-1]-propanol-(2)

1-(3,5-dimethyl-phenoxy)-3-[1,1-dimethyl-3-(N-benzimidazolonyl)-propylamino-1]-propanol-(2)

1-(2-bromo-phenoxy)-3-[(1-methyl-2-N-benzimidazolonyl)-ethylamino-1]-propanol-(2)

1-(3-methyl-phenoxy)-3-[1-methyl-2-(N-benzimidazolonyl)ethylamino-1]-propanol-(2)

1-(2,4-dichloro-phenoxy)-3-[1-methyl-2-(N-benzimidazolonyl)-ethyl-amino-1]-propanol-(2)

1-(4-chlorophenoxy)-3-[1,1-dimethyl-3-(N-1,2,3,4-tetrahydroquinolonyl-propylamino]-propanol-(2)

A compound with antidepressive properties is, for example, 1-(2,6-dichloro-phenoxy)-3-(N-benzimidazolonyl-3-propylamino-1)-propanol-(2).

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powers, solutions, suspensions, emulsions, syrups, suppositories and the like. One effective dosage unit of the compounds according to the present invention is from 0.016 to 8.34 mgm/kg body weight, preferably 0.033 to 3.34 mgm/kg body weight per os or 0.016 to 0.34 mgm/kg body weight parenterally.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 30

Tablets

The tablet composition is compounded from the following ingredients:

| | |
|---|---|
| 1-(2-Cyano-phenoxy)-3-[(1,1-dimethyl-4-N-benzimidazolone(2)yl)-butyl-amino-1]-propanol-(2) . HCl | 40.0 parts |
| Corn starch | 164.0 parts |
| Sec. calciumphosphate | 240.0 parts |
| Magnesium stearate | 1.0 parts |
| Total | 445.0 parts |

Preparation:

The ingredients are intimately admixed with each other, the mixture is granulated in conventional manner, and the granulate is compressed into 445 mgm-tablets. Each tablet is an oral dosage unit composition containing 40 mgm of the active ingredient.

EXAMPLE 31

Gelatin capsules

The capsule filler composition is compounded from the following ingredients:

| | |
|---|---|
| 1-(4-Hydroxy-phenoxy)-3-[1,1-dimethyl-3-(3-phenylimidazolidinone(2)yl)-propylamino-1]-2-propanol-(2) oxalate | 25.0 parts |
| Corn starch | 175.0 parts |
| Total | 200.0 parts |

Preparation:

The ingredients are intimately admixed with each other, and 200 mgm-portions of the mixture are filled into gelatin capsules of suitable size. Each capsule is an oral dosage unit composition containing 25 mgm of the active ingredient.

EXAMPLE 32

Coated sustained-release pills

The pill core composition is compounded from the following ingredients:

| | |
|---|---|
| 1-($\alpha$-Naphthoxy)-3-[1,1-dimethyl-3-(N-benzimidazolone(2)yl)-propylamino-(1)]-propanol-(2) . HCl | 25.0 parts |
| Carboxymethyl cellulose (CMC) | 295.0 parts |
| Stearic acid | 20.0 parts |
| Cellulose acetate phthalate (CAP) | 40.0 parts |
| Total | 380.0 parts |

Preparation:

The active ingredient, the CMC and the stearic acid are intimately admixed and the mixture is granulated in the usual way, using a solution of the CAP in 200 ml of a mixture of ethanol/ether acetate as the moistening agent. Then, the granulate is compressed into 380 mgm-pill cores which are subsequently coated in the conventional way by means of a sugary 5% solution of polyvinylpyrrolidone in water. Each coated pill contains 25 mgm of the active ingredient.

EXAMPLE 33

Tablets with combination of active ingredients

The tablet composition is compounded from the following ingredients:

| | |
|---|---|
| (−)-1-($\alpha$-Naphthoxy)-3-[1,1-dimethyl-3-(N)-benzimidazolone(2)-yl)-propylamino-(1)]-propanol-(2) . HCl | 35.0 parts |
| 2,6-Bis-(diethanolamino)-4,8-dipiperidino-pyrimido-[5,4-d]-pyrimidine | 75.0 parts |
| Lactose | 164.0 parts |
| Corn starch | 194.0 parts |
| Colloidal silicic acid | 14.0 parts |
| Polyvinylpyrrolidone | 6.0 parts |
| Magnesium stearate | 2.0 parts |
| Soluble starch | 10.0 parts |
| Total | 500.0 parts |

Preparation:

After admixing the active ingredients throughly with the lactose, the corn starch, the colloidal silicic acid and the polyvinylpyrrolidone, the mixture is granulated in the conventional way, using an aqueous solution of the

We claim:

1. A compound of the formula

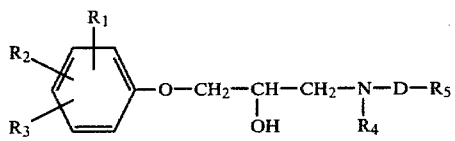

wherein $R_1$ is hydrogen; halogen; trifluoromethyl; nitro; alkyl of 1 to 8 carbon atoms; alkoxy of 1 to 4 carbon atoms; alkoxyalkyl of 2 to 8 carbon atoms; alkenyl of 2 to 5 carbon atoms; alkynyl of 2 to 5 carbon atoms; alkenyloxy of 3 to 6 carbon atoms; alkynyloxy of 3 to 6 carbon atoms; —$(CH_2)_x$—A', where x is 1, 2 or 3 and A' is cyano, amino, carboxamido or hydroxyl; phenoxy, naphthoxy, benzyloxy or —$CH_2$—$SO_2$—$CH_3$;

$R_2$ is hydrogen; halogen; alkyl of 1 to 4 carbon atoms; alkoxy of 1 to 4 carbon atoms; aralkoxy of 7 to 14 carbon atoms; alkenyl of 2 to 4 carbon atoms; nitro; or, together with $R_3$, —CH=CH—CH=CH— which is attached to carbon atoms of the phenyl ring in the o-position with respect to each other;

$R_3$ is hydrogen; halogen; alkyl of 1 to 4 carbon atoms; alkoxy of 1 to 4 carbon atoms; or aralkoxy of 7 to 14 carbon atoms;

$R_4$ is hydrogen; alkyl of 1 to 5 carbon atoms; or aralkyl of 7 to 14 carbon atoms;

$R_5$ is

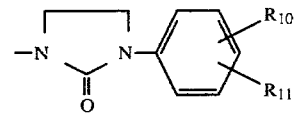

where $R_{10}$ and $R_{11}$ are each hydrogen, halogen, alkyl of 1 to 4 carbon atoms, alkoxy of 1 to 4 carbon atoms, trifluoromethyl, carboxamido or, together with each other, —O—$(CH_2)_y$—O—, where y is 1 or 2, attached to carbon atoms of the phenyl ring in o-position with respect to each other; and D is alkylene of 1 to 12 carbon atoms, or a non-toxic, pharmacologically acceptable acid addition salt thereof.

2. The compound of claim 8, wherein $R_2$ is benzyloxy.

3. The compound of claim 1, wherein $R_3$ is benzyloxy.

4. A compound of claim 1, which is 1-(2,4-dichlorophenoxy)-3-[1,1-dimethyl-2-(3-phenyl-imidazolidinon(2)-yl)-ethyl-amino-1]-propanol-(2) or a non-toxic, pharmacologically acceptable acid addition salt thereof.

5. An α- and β-adrenolytic pharmaceutical dosage composition consisting essentially of an inert pharmaceutical carrier and an effective amount of a compound of claim 1.

6. The method of blocking the α- and β-adrenergic receptors in a warm-blooded animal in need thereof, which comprises perorally, parenterally or rectally administering to said animal an effective amount of a compound of claim 1.

7. An α-and β-adrenoylytic pharmaceutical dosage composition consisting essentially of an inert pharmaceutical carrier and an effective amount of a compound of claim 4.

8. The method of blocking the α-and β-adrenergic receptors in a warm-blooded animal in need thereof, which comprises perorally, parenterally or rectally administering to said animal an effective amount of a compound of claim 4.

UNITED STATES PATENT AND TRADEMARK OFFICE
CERTIFICATE OF CORRECTION

PATENT NO. : 4,256,756                                        Page 1 of 2

DATED      : March 17, 1981

INVENTOR(S) : HERBERT KÖPPE ET AL.

It is certified that error appears in the above—identified patent and that said Letters Patent is hereby corrected as shown below:

Preamble page, under [54]; and Column 1, second line of title:

"DONIDAZALIDINON-2-YL" should read

-- IMIDAZOLIDINON-2-YL --.

Column 1, line 36: "-N-" should read -- -NH- --.

lines 37 and 49: Delete "H-".

line 48: "CO-N-" should read -- -CO-NH- --.

line 49: "-CH-" should read -- -CH$_2$- --.

line 50: Delete "$_2$-".

Column 15, Table IV: "2-O-CH$_2$-C=CH" should read

-- 2-O-CH$_2$-C≡CH --.

Column 15, line 59; and Column 16, line 10: "chloroe-" should read -- chloro- --.

Column 15, line 60; and Column 16, line 11: "thyl)" should read -- ethyl) --.

UNITED STATES PATENT AND TRADEMARK OFFICE
CERTIFICATE OF CORRECTION

PATENT NO. : 4,256,756

DATED : March 17, 1981

INVENTOR(S) : HERBERT KÖPPE ET AL.

It is certified that error appears in the above—identified patent and that said Letters Patent is hereby corrected as shown below:

Column 17, lines 39 and 62: "-epox-" should read

-- -epoxy- --.

lines 40 and 63: "ypropane" should read -- propane --

Column 38, line 1 of claim 2: "8" should read -- 1 --.

Signed and Sealed this

Thirtieth Day of June 1981

[SEAL]

Attest:

RENE D. TEGTMEYER

Attesting Officer

Acting Commissioner of Patents and Trademarks